US010952966B2

(12) United States Patent
Farah et al.

(10) Patent No.: US 10,952,966 B2
(45) Date of Patent: Mar. 23, 2021

(54) PHARMACEUTICAL COMPOSITION COMPRISING SOLID DISPERSION OF BCS CLASS II DRUGS WITH GELUCIRES

(71) Applicant: GATTEFOSSE INDIA PVT. LTD., Mumbai (IN)

(72) Inventors: Nabil Farah, Sant-Priest (FR); Sunil Bambarkar, Mumbai (IN); Vincent Jannin, Saint-Priest (FR); Chhanda Kapadia, Mubai (IN); Mangal Nagarsenker, Mumbai (IN); Meenakshi Venkataraman, Mumbai (IN); Megha Marwah, Mumbai (IN)

(73) Assignee: Gattefosse India Pvt. Ltd., Mumbai (IN)

( * ) Notice: Subject to any disclaimer, the term of this patent is extended or adjusted under 35 U.S.C. 154(b) by 0 days.

(21) Appl. No.: 15/400,539

(22) Filed: Jan. 6, 2017

(65) Prior Publication Data

US 2017/0119671 A1 May 4, 2017

Related U.S. Application Data

(63) Continuation-in-part of application No. PCT/IN2015/000275, filed on Jul. 6, 2015.

(30) Foreign Application Priority Data

Jul. 6, 2014 (IN) .......................... 1874/MUM/2014

(51) Int. Cl.
*A61K 9/16* (2006.01)
*A61K 9/20* (2006.01)
*A61K 31/4184* (2006.01)
*A61K 9/14* (2006.01)
*A61J 3/10* (2006.01)

(52) U.S. Cl.
CPC ............... *A61K 9/1617* (2013.01); *A61J 3/10* (2013.01); *A61K 9/145* (2013.01); *A61K 9/1611* (2013.01); *A61K 9/1652* (2013.01); *A61K 9/1682* (2013.01); *A61K 9/2009* (2013.01); *A61K 9/2013* (2013.01); *A61K 9/2054* (2013.01); *A61K 9/2059* (2013.01); *A61K 31/4184* (2013.01)

(58) Field of Classification Search
CPC ........ A61K 31/4184; A61K 9/14; A61K 9/20; A61K 9/16; A61K 9/2027; A61K 9/2853
See application file for complete search history.

(56) References Cited

U.S. PATENT DOCUMENTS

2001/0051134 A1* 12/2001 Pandya ..................... A23L 2/40
424/44
2009/0074859 A1 3/2009 Mahesh

FOREIGN PATENT DOCUMENTS

| IN | 2010MU0083 | * | 11/2012 | |
| IN | 201000083 | * | 11/2012 | ......... A61K 31/4184 |
| WO | WO 2006113631 A2 | * | 10/2006 | .............. A61K 9/145 |
| WO | WO 2008084504 A2 | * | 7/2008 | ........... A61K 9/0065 |
| WO | WO-2008084504 A2 | * | 7/2008 | ........... A61K 9/0065 |
| WO | 2013/0105026 A1 | | 7/2013 | |

OTHER PUBLICATIONS

Beg et al., AAPS PharmSciTech vol. 13 pp. 1416-1428. Published 2012.*
Gelucire 50/13 product page. Gattefosse. Published 2010.*
Shohin et al., (Journal of Pharmaceutical Sciences vol. 103 pp. 367-377. Published Feb. 2014; abstract, p. 267, p. 373-374).*
Elmalehm H. el al., Probe into the physical properties of a Gelucire 44/14 pharmaceuitcal formulation. Published online 2014.*
Beg et al (AAPS PharmSciTech vol. 13, pp. 1416-1427, Published 2012).*
Michenaud, M. et al Thesis for doctor in Pharmacy. Pubilshed Oct. 14, 2013.*
Elmaleh et al (Probe into the Physical Properties of a Gelucire 44/14 Pharmaceutical formulation) (Year: 2003).*
N'Diaye et al (International Journal of Pharmaceutics vol. 254 pp. 263-269. Published 2003). (Year: 2003).*
Aksu et al (African Journal of Pharmacy and Pharmacology vol. 7 pp. 2201-2209. Published 2013). (Year: 2013).*
Michenaud et al (Thesis for the doctor in Pharmacy published Oct. 14, 2013). (Year: 2013).*
Park et al., (International Journal of Pharmaceutics vol. 441 pp. 50-55. Published online Dec. 20, 2012). (Year: 2012).*
Elmaleh et al., (Probe into the Physical Properties of a Gelucire 44/14 Pharmaceutical formulation). Published 2003. (Year: 2003).*
Park et al., (Arch Pharm Res vol. 34 pp. 463-468. Published 2011) (Year: 2011).*
N'Diaye et al (International Journal of Pharmaceutics vol. 254 published 263-269, published 2003) (Year: 2003).*
Aksu (African Journal of Pharmacy and Pharmacology vol. 7 pp. 2201-2209, published 2013 (Year: 2013).*
Michenaud et al (Thesis for the doctor in pharmacy published Oct. 14, 2013; translation provided) (Year: 2013).*
Shohin et al., (Journal of Pharmaceutical Sciences vol. 103 pp. 367-377. Published Feb. 2014 (Year: 2014).*
Elmaleh (Probe into the Physical Properties of a Gelucire 44/14 Pharmaceutical formulation, published 2003), (Year: 2003).*
Written Opinion of the International Searching Authority and International Search Report dated Jan. 14, 2016 for PCT/IN2015/000275.

* cited by examiner

Primary Examiner — Timothy P Thomas
Assistant Examiner — George W Kosturko
(74) Attorney, Agent, or Firm — Kramer Amado

(57) ABSTRACT

A solid pharmaceutical composition comprising a solid dispersion of a BCS Class II drug in a solid carrier/hydrophilic carrier; and a pH modifier. The solid carrier/hydrophilic carrier has a melting point of between about 40° C. to about 60° C. and an HLB value of between about 10 and about 18. The BCS Class II drug may be telmisartan.

8 Claims, 5 Drawing Sheets

PHARMACEUTICAL COMPOSITION COMPRISING SOLID DISPERSION OF BCS CLASS II DRUGS WITH GELUCIRES

CROSS-REFERENCE TO RELATED APPLICATIONS

This application is a continuation-in-part of parent International Application No. PCT/IN2015/000275, filed on Jul. 6, 2015 and published as WO 2016/005994. The disclosure of the prior application is incorporated by reference herein in its entirety.

TECHNICAL FIELD OF THE INVENTION

The present invention relates to pharmaceutical composition comprising of solid dispersion of BCS (Biopharmaceutics Classification System) class II drugs in a novel pharmaceutical carrier. More particularly, the invention relates to pharmaceutical composition comprising solid dispersion of BCS class II drugs in Gelucires.

BACKGROUND AND PRIOR ART

The Biopharmaceutical Classification System (BCS) is a system to differentiate the drugs on the basis of their solubility and permeability. According to this classification, the drugs are placed under four classes based on their solubility and permeability.

The drugs which are of high permeability and low solubility are classified under class II. The bioavailability of these drugs is limited by their dissolution rate. Drug delivery systems are designed to improve oral bioavailability of BCS class II drugs. Improving oral bioavailability of BCS class II drugs as solid dosage forms remains a challenge for the formulation scientists. Therefore there is a continuous research in the art for developing variety of drug delivery systems to improve the solubility of poorly soluble drugs, such as, self-emulsifying systems (SEDDS); self-nano emulsifying systems (SNEDDS); oral lipid based drug delivery systems; nanoparticulate drug delivery systems; polymer systems; solid dispersions etc.

Among the various approaches to improve solubility, the solid dispersion technique has often proved to be successful in improving the dissolution and bioavailability of poorly soluble drugs because it is simple, economic, and advantageous. Solid dispersion technique improves the dissolution rate of highly lipophilic drugs by reducing drug particle size, improving wettability and forming amorphous particles.

The term solid dispersion refers to a group of solid products consisting of uniformly mixed inert carrier and drug. The carrier can either be crystalline or amorphous in nature. Most commonly used carriers for the preparation of solid dispersions consist of excipients like polyethylene glycols (PEGs), polyvinylpyrrolidone (PVPs), Gelucires, sugars, saccharides, urea or mixtures thereof. The drug can be dispersed either molecularly or as amorphous/crystalline particles.

Telmisartan (TEL) is one such BCS class II drug, exhibiting pH dependent solubility. TEL is manufactured and supplied in the free acid form and is characterized by poor solubility resulting in low bioavailability. It is readily ionizable exhibiting maximum solubility at high and low pH (pH 3 to 9: poorly soluble). pH modifier like meglumine has been employed, to improve solubility of TEL. Literature provides with the use of pH modifiers like citric acid, tartaric acid, malic acid, sodium carbonate, potassium hydroxide for altering the microenvironmental pH of TEL improving its solubility and hence dissolution. However, it is reported that TEL degrades in strong alkaline conditions thereby limiting the use of the latter.

In addition to a pH dependent solubility profile, TEL is a lipophilic compound with a partition coefficient, log P=3.2 (n-octanol: buffer pH 7.4). Reports suggest the use of excipients such as polyethylene glycol, Polyvinyl pyrrolidone, Poloxamers and the like which improve solubility and dissolution of poorly soluble drugs like TEL.

The solid dispersions are prepared conventionally using the methods selected from fusion (melt), solvent evaporation, spray drying, lyophilization (freeze drying), hot-melt-extrusion, electrostatic spinning method, coating on sugar beads using fluidized bed coating system, supercritical fluid technology. Despite the commendable research in the field of solid dispersion in the past four decades, the commercial utilization of the same is very limited due to the problems involved such as physical and chemical stability of drugs and carriers; reproducibility of physicochemical properties of such carriers; further formulating solid dispersions into dosage forms; scaling up such processes, and the like.

Therefore, there is need to provide oral pharmaceutical dosage form of BCS class II drugs comprising stable solid dispersions with improved solubility. In addition there is also a need to provide simple methods of preparation that can be scaled to industrial levels. Hence, the objective of the present invention is to provide oral pharmaceutical compositions comprising stable solid dispersion of BCS class II drugs with improved dissolution and potential to improve bioavailability for which protection is sought.

SUMMARY OF THE INVENTION

In accordance with the above objective, the present invention provides pharmaceutical compositions comprising solid dispersions of BCS class II drug dispersed in a Gelucires (polyethylene glycol glycerides composed of mono- and di esters of polyethylene glycol). One preferred BCS class II drug according to the invention is TEL.

Accordingly, in a preferred aspect, the invention provides pharmaceutical composition comprising solid dispersion of TEL dispersed in Gelucires such as Gelucire® 44/14, Gelucire® 50/13 and Gelucire® 48/16. Gelucire® 48/16 is hitherto unemployed solid carrier in the preparation of solid dispersions.

In another aspect, the solid dispersion prepared according to the invention can be formulated as different dosage forms either by encapsulating in a hard gelatin capsule or by granulating using suitable pharmaceutical excipients followed by compression into a tablet.

DETAILED DESCRIPTION OF THE INVENTION

Figure 1:
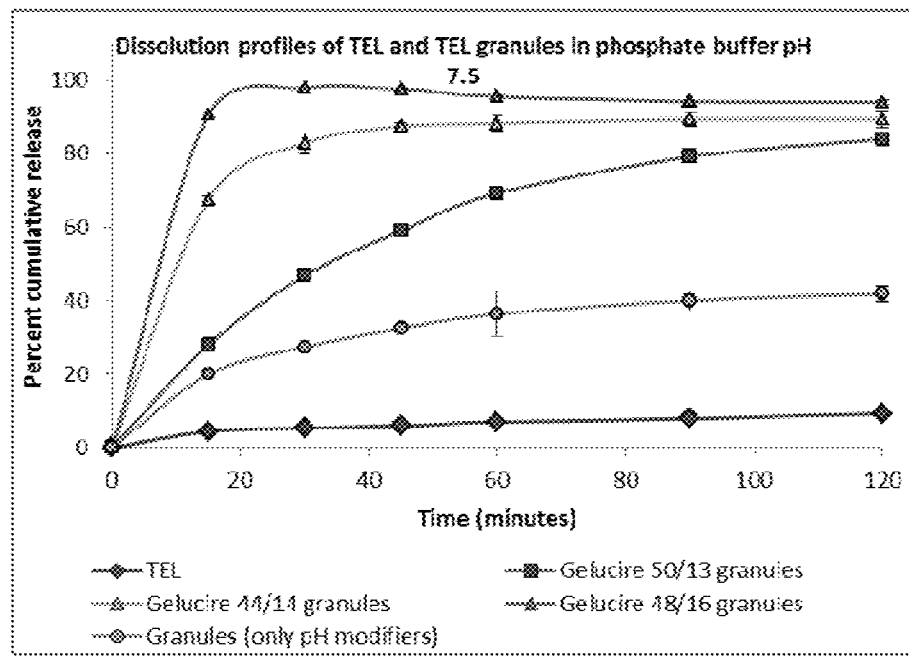
FIG. 1 depicts dissolution profiles of TEL and granules of TEL in phosphate buffer pH 7.5.
Figure 2:
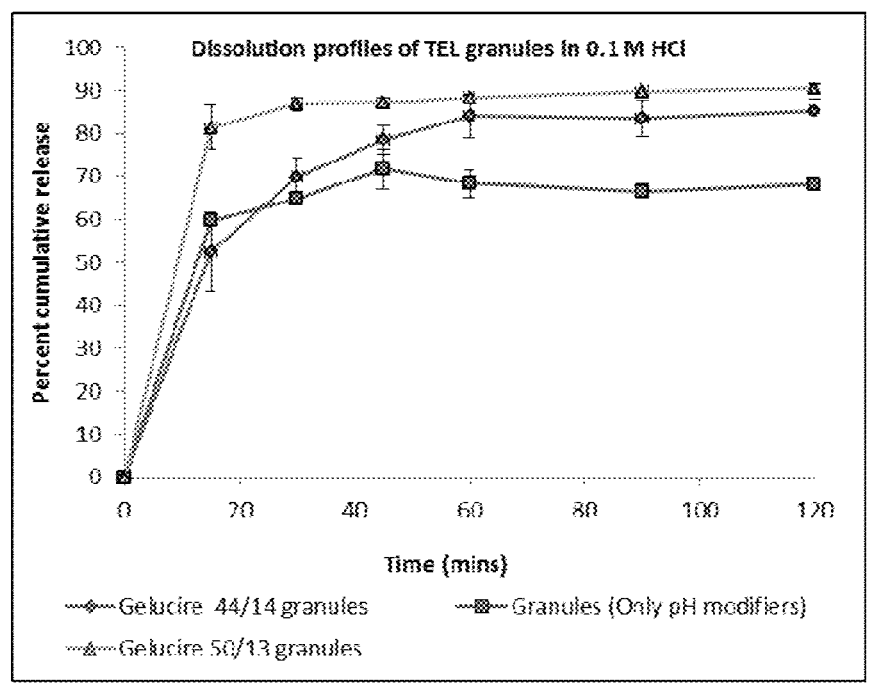
FIG. 2 depicts dissolution profiles of TEL and granules of TEL in 0.1 M HCl.
Figure 3:
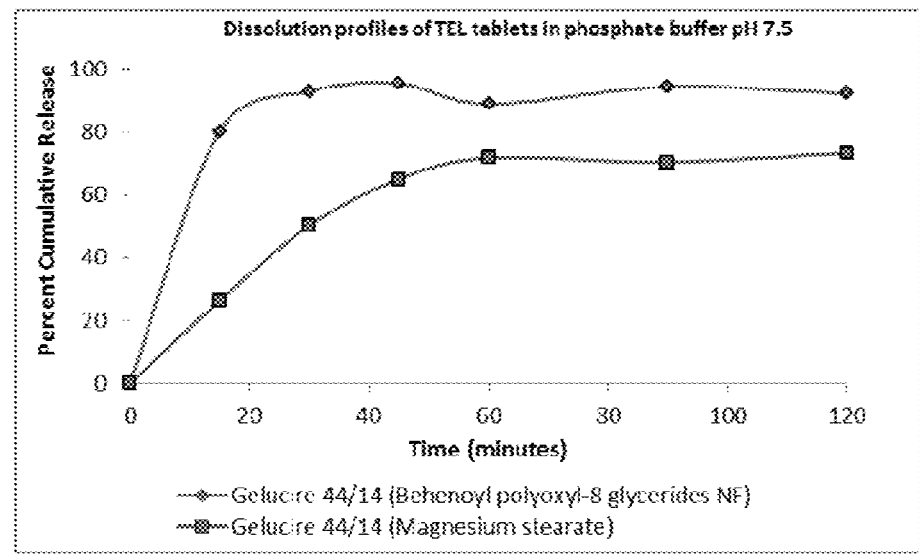
FIG. 3 depicts dissolution profiles in phosphate buffer pH 7.5 of TEL tablets containing lauroyl polyoxyl-32 glycerides NF (Gelucire® 44/14).
Figure 4:
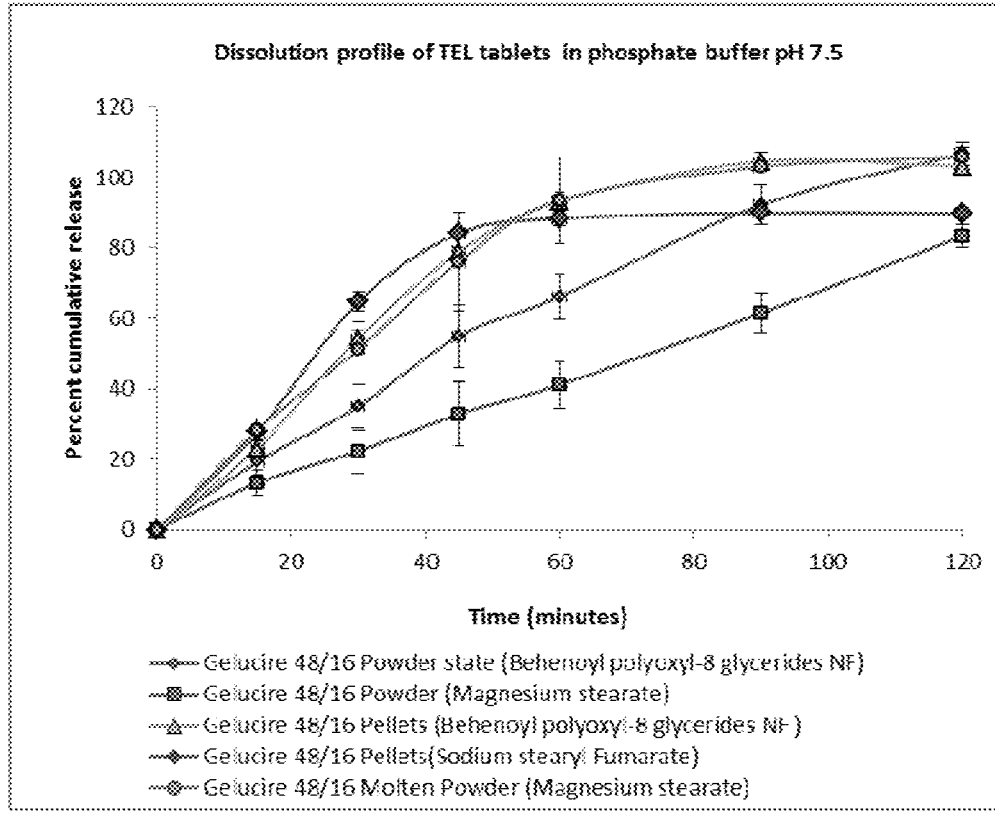
FIG. 4 depicts dissolution profiles in phosphate buffer pH 7.5 of TEL tablets containing PEG-32-stearate (Gelucire® 48/16).

The invention will now be described in detail in connection with certain preferred and optional embodiments, so that various aspects thereof may be more fully understood and appreciated.

The present invention provides a pharmaceutical composition comprising solid dispersion of BCS class II drug in Gelucires with pH modifiers using a novel process. Gelucires are polyethylene glycol (PEG) glycerides composed of mono- and di esters of polyethylene glycol. Gelucire® 48/16, a novel carrier available in powder and pellet forms, is PEG-32 stearate, while, conventional gelucires, Gelucire® 44/14 and Gelucire® 50/13 are lauroyl polyoxyl-32glycerides NF and stearoyl polyoxyl-32 glycerides NF respectively. One preferred BCS class II drug is TEL.

The solid carriers used in the present invention are hydrophilic with a low melting point in the range of 40° C. to 60° C. with HLB value between 10-18. Gelucires aid in solubility by improving the wettability of BCS class II drugs with poor solubility profile via its surface active properties forming a fine emulsion owing to its self-emulsifying behavior.

Accordingly, in a preferred embodiment, the invention provides a solid pharmaceutical composition comprising solid dispersion of BCS Class II drug, TEL, in solid carrier/hydrophilic carrier with pH modifiers wherein said solid carrier/hydrophilic carrier having low melting point in the range of 40° C. to 60° C. with HLB value between 10-18.

In another preferred embodiment, the invention provides pharmaceutical composition comprising solid dispersion of TEL dispersed in Gelucires. The novel carrier of the invention, Gelucire® 48/16, enables the preparation of solid dispersion as simple as admixing and thus avoids the need for tedious manufacturing methods and equipment reported in the prior art which is an added advantage over conventional Gelucires.

According to typical embodiment, the invention provides solid dispersion granules of TEL in Gelucire® 48/16 (PEG-32-stearate) with pH modifiers and solid dispersion of TEL in conventional carriers, Gelucire® 44/14, (which is composed of mixture of PEG-esters i.e.PEG-32 glyceryl laurate, a small glyceride fraction and free PEG)/Gelucire® 50/13 (composed of palmitoyl and stearoyl esters of glycerol, PEG esters and free PEG) with pH modifiers have been prepared and further formulated as tablets using tableting excipients selected from granulating agents, binders, lubricants, glidants, super disintegrants, diluents, adsorbents and the like.

The pH modifiers used according to the invention are selected from the group consisting of sodium hydroxide (NaOH), sodium bicarbonate (NaHCO$_3$), magnesium oxide (MgO), potassium hydroxide, meglumine, sodium carbonate, citric acid, tartaric acid, ascorbic acid and malic acid.

Granulating agent/binder(s) are selected from starch, gums (inclusive of natural, semisynthetic and synthetic), microcrystalline cellulose, ethyl cellulose, methyl cellulose, liquid glucose polymers such as povidone and the like.

The lubricants are selected from the group consisting of magnesium stearate, glyceryl esters, behenoyl polyoxyl-8 glycerides Nf (Compritol HD5 ATO), sodium stearyl fumarate and the like, preferably, behenoyl polyoxyl-8 glycerides NF.

Super disintegrants are selected from synthetics like sodium starch glycollate, cross povidone, cross carmellose sodium, kollidon CL, and natural origin such as locust bean gum and the like.

Glidants are selected from talc, magnesium stearate, colloidal silicon dioxide, starch and the like.

The diluents are selected from dextrose, lactose, mannitol, microcrystalline cellulose, sorbitol, sucrose, dibasic calcium phosphate, calcium suphate dihydrate.

The adsorbents are selected from silicon dioxide, purified aluminium silicate and the like.

The pharmaceutical composition of the present invention can be formulated as different dosage forms such as tablet, capsule or granule.

In another typical embodiment, the invention provides a process for preparation of pharmaceutical composition wherein the processing of the granules employing melt granulation and the process steps comprises melting/mixing of a solid carrier/hydrophilic carrier with dispersion of BCS class II drug in pH modifier solution in the presence of diluents.

In another typical embodiment, the invention provides a process for preparation of pharmaceutical composition wherein the processing of the solid dosage form employing both melt and wet granulation. Said process steps comprises, a) melting/mixing of a solid carrier/hydrophilic carrier with dispersion of BCS class II drug in pH modifier solution;

b) granulating step (a) using binders in presence of diluents;

c) mixing super disintegrants, lubricants with granules obtained in step (b);

d) compressing granules obtained in step (c) in controlled temperature and humidity conditions to get tablets with good integrity.

Accordingly, in another embodiment, the present invention discloses a solid pharmaceutical dosage form being granules composed of BCS class II drug like TEL, in solid carrier/hydrophilic carrier gelucire such as lauroyl polyoxyl-32 glycerides NF (Gelucire® 44/14) having melting point 44° C. and HLB value 14 along with pH modifiers like sodium hydroxide, sodium bicarbonate, magnesium oxide, potassium hydroxide, meglumine, sodium carbonate, citric acid, tartaric acid, ascorbic acid, malic acid; diluents like dextrose, lactose, mannitol, microcrystalline cellulose, sorbitol, sucrose, Dibasic calcium phosphate and calcium sulphate dihydrate.

In another embodiment, the present invention discloses a solid pharmaceutical dosage form being granules composed of BCS class II drug like TEL, in solid carrier/hydrophilic carrier gelucire such as stearoyl polyoxyl-32 glycerides (Gelucire® 50/13) having melting point 50° C. and HLB value 13 along with pH modifiers like sodium hydroxide, sodium bicarbonate, magnesium oxide, potassium hydroxide, meglumine, sodium carbonate, citric acid, tartaric acid, ascorbic acid, malic acid; diluents like dextrose, lactose, mannitol, microcrystalline cellulose, sorbitol, sucrose, Dibasic calcium phosphate and calcium sulphate dihydrate.

In another embodiment, the present invention discloses a solid pharmaceutical dosage form being granules composed of BCS class II drug like TEL, in solid carrier/hydrophilic carrier Gelucire such as PEG-32-stearate (Gelucire® 48/16) having melting point 48° C. and HLB value 16 with pH modifiers like sodium hydroxide, sodium bicarbonate, magnesium oxide, potassium hydroxide, meglumine, sodium carbonate, citric acid, tartaric acid, ascorbic acid, malic acid; diluents like dextrose, lactose, mannitol, microcrystalline cellulose, sorbitol, sucrose, dibasic calcium phosphate and calcium sulphate dihydrate.

In another embodiment, the present invention discloses a solid pharmaceutical dosage form being tablets composed of BCS class II drug like TEL, in solid carrier/hydrophilic carrier gelucire such as lauroyl polyoxyl-32 glycerides NF (Gelucire® 44/14) having melting point 44° C. and HLB value 14 along with pH modifiers like sodium hydroxide, sodium bicarbonate, magnesium oxide, potassium hydroxide, meglumine, sodium carbonate, citric acid, tartaric acid, ascorbic acid, malic acid; diluents like dextrose, lactose, mannitol, microcrystalline cellulose, sorbitol, sucrose, dibasic calcium phosphate, calcium sulphate dihydrate; binders/granulating agents like starch, gums (natural, semi synthetic and synthetic), ethyl cellulose, polymers; super disintegrants like sodium starch glycollate, cross povidone, cross carmellose sodium, kollidon CL; lubricants like magnesium stearate, behenoyl polyoxyl-8 glycerides NF (Compritol HD5ATO) and sodium stearyl fumarate.

In another embodiment, the present invention discloses a solid pharmaceutical dosage form being tablets composed of BCS class II drug like TEL, in solid carrier/hydrophilic carrier in gelucire such as PEG-32 stearate (Gelucire® 48/16) having melting point 48° C. and HLB value 16 with pH modifiers like sodium hydroxide, sodium bicarbonate, magnesium oxide, potassium hydroxide, meglumine, sodium carbonate, citric acid, tartaric acid, ascorbic acid, malic acid; diluents like dextrose, lactose, mannitol, microcrystalline cellulose, sorbitol, sucrose, dibasic calcium phosphate, calcium sulphate dihydrate; binders/granulating agents like starch, gums (natural, semi synthetic and synthetic), ethyl cellulose, polymers; super disintegrants like sodium starch glycollate, cross povidone, cross carmellose sodium, kollidon CL; lubricants like magnesium stearate, behenoyl polyoxyl-8 glycerides NF (Compritol HD5ATO) and sodium stearyl fumarate.

In another embodiment, the present invention discloses a solid pharmaceutical dosage form being tablets composed of BCS class II drug like TEL, in solid carrier/hydrophilic carrier in gelucire such as stearoyl polyoxyl-32 glycerides NF (Gelucire® 50/13) having melting point 50° C. and HLB value 13 with pH modifiers like sodium hydroxide, sodium bicarbonate, magnesium oxide, potassium hydroxide, meglumine, sodium carbonate, citric acid, tartaric acid, ascorbic acid, malic acid; diluents like dextrose, lactose, mannitol, microcrystalline cellulose, sorbitol, sucrose, dibasic calcium phosphate, calcium sulphate dihydrate; binders/granulating agents like starch, gums (natural, semi synthetic and synthetic), ethyl cellulose, polymers; super disintegrants like sodium starch glycollate, cross povidone, cross carmellose sodium, kollidon CL; lubricants like magnesium stearate, behenoyl polyoxyl-8 glycerides NF (Compritol HD5ATO) and sodium stearyl fumarate.

Figure 5:
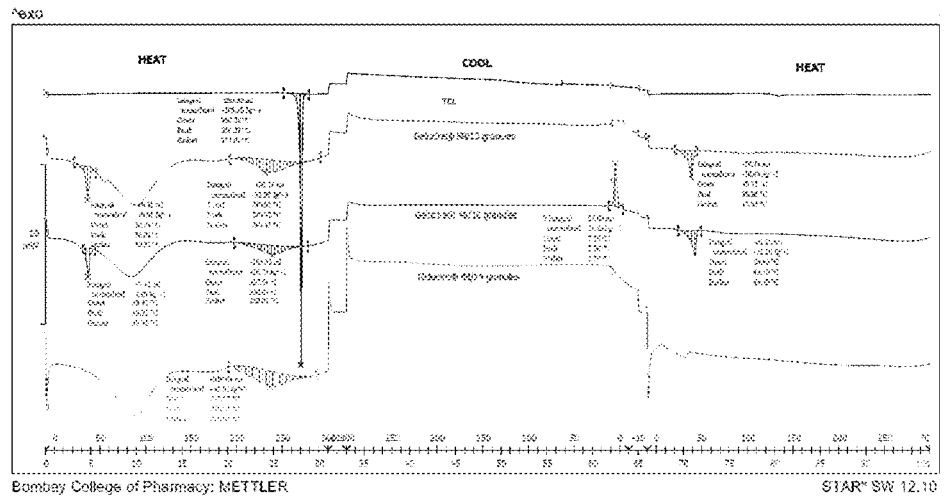
FIG. 5 shows Differential Scanning calorimetric (DSC) analysis of TEL and its formulations.
Figure 6:
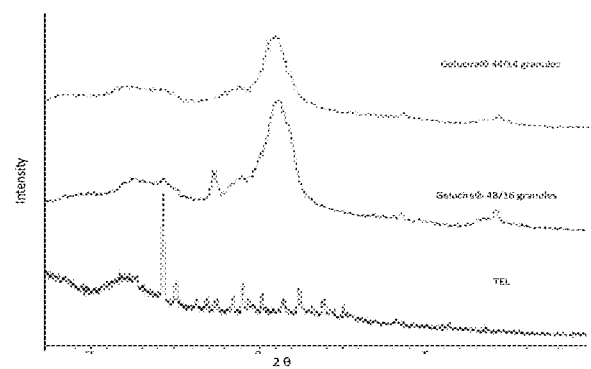
FIG. 6 shows X-Ray Diffractometric (XRD) evaluation of TEL and its formulations.

The granules of TEL in Gelucire® 48/16, TEL in Gelucire® 44/14/Gelucire® 50/13 and the compressed tablets of TEL in Gelucire® 48/16 and TEL in Gelucire® 44/14 prepared as above were subjected to dissolution studies (FIGS. 1 to 4). From the dissolution profile, it is evident that all three Gelucires aid in dissolution of TEL to the same extent by improving the wettability of the drug via their surface active properties. Further, owing to their self-emulsifying behavior, Gelucires form fine emulsion which enhances solubility of TEL. The amorphisation of TEL in formulations also aids in solubilisation which is confirmed by DSC and XRD (FIGS. 5 and 6). Further, the pH modifiers aid dissolution by altering the microenvironmental pH of the drug. Stress degradation studies performed on plain TEL drug in 1 N NaOH at 80° C. for 8 hours revealed 64.4% reduction in area on analysis by stability indicating HPLC method. The pH modifiers employed were in low concentration at which no TEL degradation was observed.

Figure 7:
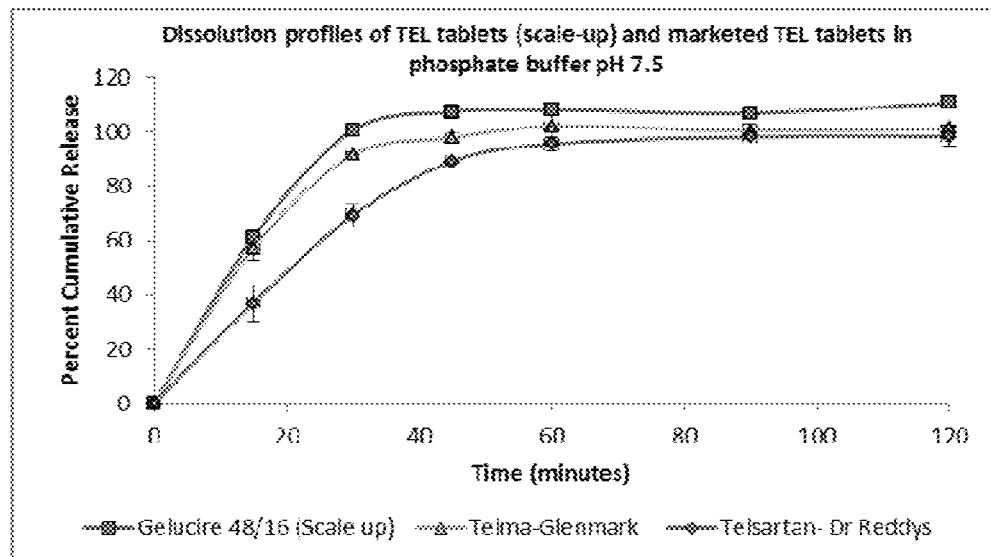
FIG. 7 depicts dissolution profiles in phosphate buffer pH 7.5 of TEL tablets containing PEG-32-stearate (Gelucire® 48/16) prepared in a scale up batch and marketed TEL tablets.
Figure 8:
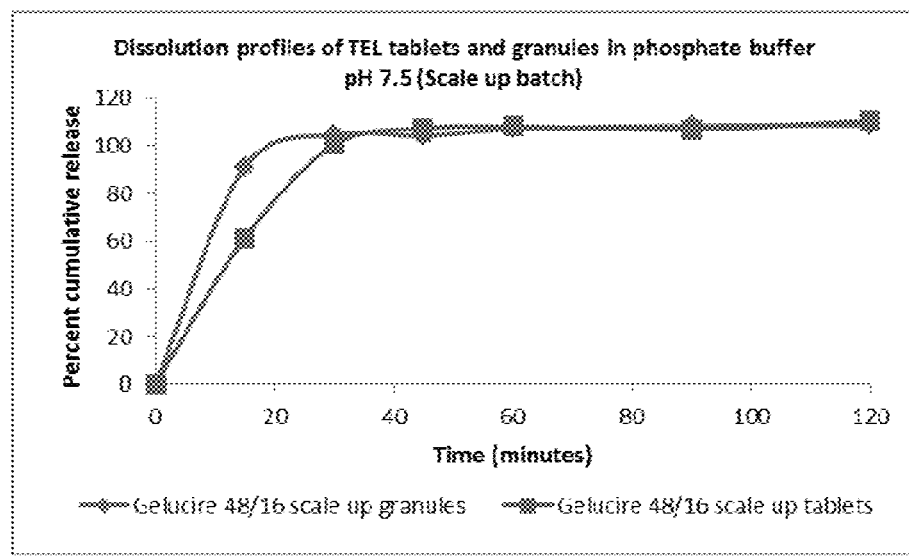
FIG. 8 depicts dissolution profiles in phosphate buffer pH 7.5 of TEL tablets and granules containing PEG-32-stearate (Gelucire® 48/16) prepared in a scale up batch.

The formula developed with Gelucires is amenable to scale up using RMG (Rapid Mixer Granulator). The dissolution profile of these tablets is superior to the dissolution profile of marketed tablets of TEL (FIG. 7). The release of TEL from granules prepared in scale up batch is equivalent to that of tablets prepared in the scale up batch (FIG. 8). The novel lubricant, behenoyl polyoxyl-8 glycerides, aids in improving dissolution of drug compared to conventional lubricants like magnesium stearate, sodium stearyl fumarate. A novel process amenable to scale up combining melt and wet granulation technique has been developed.

The present invention discloses the drug release of a solid pharmaceutical dosage form i.e. granules and tablets, which are given below in Table 1 and Table 2 as follows.

TABLE 1

Dissolution data of TEL granules
Time: 2 hours

| Sr. No. | Dosage form | Gelucire Type | % Release of drug | Medium |
|---|---|---|---|---|
| 1. | Granules | Only pH modifiers | Not less than 40% and not more than 45% | pH 7.5 phosphate buffer |
| 2. | Granules | pH modifiers and gelucire | Not less than 80% and not more than 100% | pH 7.5 phosphate buffer |
| 3. | Granules | Only pH modifiers | Not more than 70% | 0.1 M HCl |
| 4. | Granules | pH modifiers and gelucire | Not less than 80% and not more than 95% | 0.1 M HCl |

TABLE 2

Dissolution data of TEL tablets
Dissolution medium: pH 7.5 phosphate buffer
Time: 2 hours

| Sr. No. | Dosage form | Gelucire type | Lubricant | % Release of drug |
|---|---|---|---|---|
| 1. | Tablets | lauroyl polyoxyl-32 glycerides NF | Magnesium stearate | Not less than 65% and not more than 75% |
| 2. | Tablets | lauroyl polyoxyl-32 glycerides NF | Behenoyl polyoxyl-8 glycerides NF | Not less than 95% |
| 3. | Tablet | PEG-32 stearate in the form of powder | Magnesium stearate | Not less than 85% |
| 4. | Tablet | PEG-32 stearate in the form of pellets | Behenoyl polyoxyl-8 glycerides NF | Not less than 95% |
| 5. | Tablet | PEG-32 stearate in the form of pellets | Sodium Stearyl Fumarate | Not less than 85% and not more than 90% |
| 6. | Tablets | PEG-32 stearate in the form of powder | Behenoyl polyoxyl-8 glycerides NF | Not less than 95% |

The present invention discloses a solid pharmaceutical dosage form wherein improvement in dissolution of BCS class II drug owing to the presence of gelucires, pH modifiers and amorphisation of drug in formulation.

The present invention discloses a solid pharmaceutical dosage form being granules that has good flow properties and compressibility The present invention discloses a solid pharmaceutical dosage form with good tableting properties comprising Gelucires.

The following examples, which include preferred embodiments, will serve to illustrate the practice of this invention, it being understood that the particulars shown are by way of example and for purpose of illustrative discussion of preferred embodiments of the invention.

Dissolution Studies

Dissolution Parameters:
The dissolution parameters are as follows:
Volume of dissolution medium—900 mL
Dissolution medium—
 a) pH 7.5 phosphate buffer USP
 b) 0.1 M HCl (IP 2010 recommendation)
Volume of aliquot—5 mL
Temperature—37° C.
Time Points—15 min, 30 min, 45 min, 60 min, 90 min, 120 min.
Differential Scanning Calorimetric Analysis:
Thermal analysis of TEL and its formulations was performed using Mettler Toledo DSC 1 Star E system. The samples were subjected to heat-cool-heat cycles in the temperature range of −10° C. to 300° C. at a heating rate of 10° C./min.
X-Ray Diffraction Studies:
XRD studies were carried out on TEL and its formulations in the scanning range of 7-70° employing Philips P Analytical X'pert Pro X ray diffractometer.
 Characterisation of Granules
 Angle of repose: 20.55°
 Flow rate: 15.8 g/sec
 Compressibility: 13%
 Hausner ratio: 1.149
 Characterisation of Tablets
 Appearance—Off white colour
 Hardness—2.5-3 kg/cm$^2$
 Thickness 3 mm
 Diameter 8.5 mm
 Friability—less than 1%
 Disintegration Time: Less than 15 minutes

EXAMPLES

Example 1

TEL granules prepared with Gelucire® 44/14

| Ingredients | Quantity |
| --- | --- |
| Crystalline TEL | 20-80 mg |
| Gelucire ® 44/14 | 40-320 mg |
| NaOH, NaHCO$_3$, MgO | 1-10 mg |
| Microcrystalline cellulose | 140-160 mg |

TEL was mixed with molten Gelucire® 44/14 and pH modifiers, followed by addition of diluents. The dough thus obtained was then sieved to get desired granule size.

Example 2

TEL granules prepared with Gelucire® 50/13

| Ingredients | Quantity |
| --- | --- |
| Crystalline TEL | 20-80 mg |
| Gelucire ® 50/13 | 40-320 mg |
| NaOH, NaHCO$_3$, MgO | 1-10 mg |
| Microcrystalline cellulose | 140-160 mg |

TEL was mixed with molten Gelucire® 50/13 and pH modifiers, followed by addition of diluents. The dough thus obtained was then sieved to get desired granule size.

Example 3

TEL granules prepared with Gelucire® 48/16 (Powder)

| Ingredients | Quantity |
| --- | --- |
| Crystalline TEL | 20-80 mg |
| Gelucire ® 48/16 | 40-320 mg |
| NaOH, NaHCO$_3$, MgO | 1-10 mg |
| Microcrystalline cellulose | 140-160 mg |

TEL was mixed with molten novel excipients Gelucire® 48./16 and pH modifiers, followed by addition of diluents. The dough thus obtained was then sieved to get desired granule size.

Example 4

TEL tablets prepared with Gelucire® 44/14 (Using Magnesium stearate as lubricant)

| Ingredients | Quantity |
| --- | --- |
| Crystalline TEL | 20-80 mg |
| Gelucire ® 44/14 | 40-320 mg |
| NaOH, NaHCO$_3$, MgO | 1-10 mg |
| Starch paste | Quantity sufficient |
| Magnesium stearate | 2-3 mg |
| Sodium starch glycollate | 10-15 mg |
| Dicalcium phosphate | 80-100 mg |
| Microcrystalline cellulose | 140-160 mg |

Example 5

Tablets prepared with Gelucire® 44/14 [using Behenoyl polyoxyl-8 glycerides NF as lubricant]

| Ingredients | Quantity |
| --- | --- |
| Crystalline TEL | 20-80 mg |
| Gelucire ® 44/14 | 40-320 mg |
| NaOH, NaHCO$_3$, MgO | 1-10 mg |
| Starch paste | Quantity sufficient |
| Behenoyl polyoxyl-8 glycerides NF | 2-3 mg |
| Sodium starch glycollate | 10-15 mg |
| Dicalcium phosphate | 80-100 mg |
| Microcrystalline cellulose | 140-160 mg |

TEL was mixed with molten Gelucire® 44/14 followed by addition of pH modifiers, granulated using appropriate granulating agent, followed by addition of diluents. The dough so obtained was then sieved to get desired granule size. To these granules, lubricants, glidants, super disintegrants, diluents were mixed and compressed to obtain tablets.

Example 6

Tablets prepared with Gelucire® 48/16 powder (Using Magnesium stearate as lubricant)

| Ingredients | Quantity |
| --- | --- |
| Crystalline TEL | 20-80 mg |
| Gelucire ® 48/16 (Powder) | 40-320 mg |
| NaOH, NaHCO$_3$, MgO | 1-10 mg |
| Starch paste | Quantity sufficient |
| Magnesium stearate | 2-3 mg |
| Sodium starch glycollate | 10-15 mg |
| Microcrystalline cellulose | 140-160 mg |

TEL was mixed with novel excipient Gelucire® 48/16 (in powder/molten state), followed by addition of pH modifiers, granulated using appropriate granulating agent, followed by addition of diluents. The dough so obtained was then sieved to get desired granule size. Lubricants, glidants, super disintegrants, and diluents were mixed with these granules and compressed to obtain tablets.

Example 7

Tablets prepared with Gelucire® 48/16 powder (Using Behenoyl polyoxyl-8 glycerides NF as lubricant)

| Ingredients | Quantity |
| --- | --- |
| Crystalline TEL | 20-80 mg |
| Gelucire ® 48/16 (Powder) | 40-320 mg |
| NaOH, NaHCO$_3$, MgO | 1-10 mg |
| Starch paste | Quantity sufficient |
| Behenoyl polyoxy1-8 glycerides NF | 2-3 mg |
| Sodium starch glycollate | 10-15 mg |
| Microcrystalline cellulose | 140-160 mg |

TEL was mixed with novel excipients Gelucire® 48/16 (in powder state), followed by addition of pH modifiers, granulated using appropriate granulating agent, followed by addition of diluents. The dough so obtained was then sieved to get desired granule size. Lubricants, glidants, super disintegrants, and diluents were mixed with these granules and compressed to obtain tablets.

Example 8

Tablets prepared with Gelucire® 48/16 pellets [using Behenoyl polyoxyl-8 glycerides NF as lubricant]

| Ingredients | Quantity |
| --- | --- |
| Crystalline TEL | 20-80 mg |
| Gelucire ® 48/16 pellets | 40-320 mg |
| NaOH, NaHCO$_3$, MgO | 1-10 mg |
| Starch paste | Quantity sufficient |
| Behenoyl polyoxy1-8 glycerides NF | 2-3 mg |
| Sodium starch glycollate | 10-15 mg |
| Microcrystalline cellulose | 140-160 mg |

Example 9

Tablets prepared with Gelucire® 48/16 pellets (using Sodium stearyl fumarate as lubricant)

| Ingredients | Quantity |
| --- | --- |
| Crystalline TEL | 20-80 mg |
| Gelucire ® 48/16 pellets | 40-320 mg |
| NaOH, NaHCO$_3$, MgO | 1-10 mg |
| Starch paste | Quantity sufficient |
| Sodium stearyl fumarate | 2-3 mg |
| Sodium starch glycollate | 10-15 mg |
| Microcrystalline cellulose | 140-160 mg |

TEL was mixed with molten novel excipient Gelucire® 48/16 pellets followed by addition of pH modifiers, granulated using appropriate granulating agent, followed by addition of diluents. The dough so obtained was then sieved to get desired granule size. Lubricants, glidants, super disintegrants, and diluents were mixed with these granules and compressed to obtain tablets.

Example 10

Tablets prepared with Gelucire® 48/16 pellets (Scale up formula)

| Ingredients | Quantity |
| --- | --- |
| Crystalline TEL | 50-200 g |
| Gelucire ® 48/16 pellets | 100-800 g |
| NaOH, NaHCO$_3$, MgO | 2.5-25 g |
| Starch paste | Quantity sufficient |
| Behenoyl polyoxy1-8 glycerides NF | 5-7.5 g |
| Sodium starch glycollate | 25-37.5 g |
| Microcrystalline cellulose | 350-400 g |

TEL was mixed with molten novel excipients Gelucire® 48/16 pellet (at 20° C. above the melting point of gelucire) followed by addition of pH modifiers in 2 L RMG at a predetermined mixing speed. The mixture was granulated at an appropriate mixing speed using granulating agent, followed by addition of diluents. The dough so obtained was then sieved to get desired granule size. Lubricants, glidants, super disintegrants, and diluents were mixed with these granules and compressed to obtain tablets.

Example 11

Tablets prepared with Gelucire 44/14 (RMG Batch)

| Ingredients | Quantity |
| --- | --- |
| Crystalline TEL | 50-200 g |
| Gelucire 44/14 | 100-800 g |
| NaOH, NaHCO3, MgO | 2.5-25 g |
| Starch Paste | Quantity sufficient |
| Behenoyl polyoxy1-8 glycerides NF | 5-20 g |
| Microcrysatlline cellulose | 350-550 g |
| Croscarmellose Sodium | 25-80 g |
| Dicalcium phosphate | 200-400 g |

Figure 9:
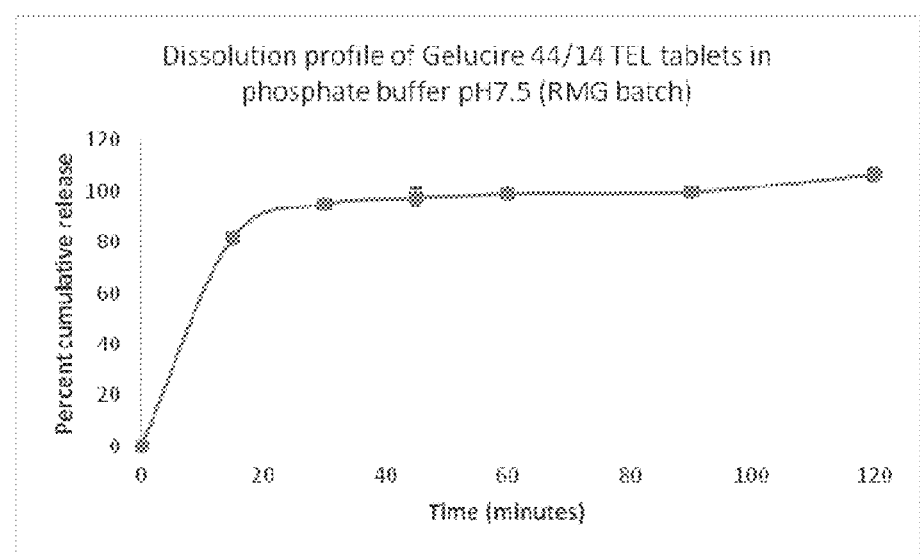
FIG. 9 depicts dissolution profiles in phosphate buffer pH 7.5 of TEL tablets prepared with Gelucire 44/14.

TEL was mixed with alkaliser solution and molten Gelucire 44/14 (at 20° C. above the melting point) in a 3 L RMG at a predetermined mixing speed. The mixture was granulated at an appropriate mixing speed using granulating agent followed by addition of diluent. The dough so obtained was then sieved to get desired granule size. Lubricants, glidants, superdisintegrants and adsorbents were mixed with these granules and compressed to obtain tablets. The dissolution profile of the resulting tablets is shown in FIG. 9.

We claim:

1. A solid pharmaceutical composition comprising:
   a solid dispersion of from 20 mg to 80 mg of telmisartan in from 40 to 320 mg of a solid carrier/hydrophilic carrier;
   from 1 to 10 mg of a basic pH modifier selected from the group consisting of sodium hydroxide (NaOH), sodium bicarbonate (NaHCO$_3$), magnesium oxide (MgO), and mixtures thereof;
   from 2 to 3 mg of behenoyl polyoxyl-8 glycerides as a lubricant;
   from 10 to 15 mg of a superdisintegrant, wherein the superdisintegrant is sodium starch glycollate;
   from 140 to 160 mg of microcrystalline cellulose; and starch paste;
   wherein said solid carrier/hydrophilic carrier has a melting point of between 40° C. and 60° C. and an HLB value of between 10 and 18; and
   wherein said solid carrier/hydrophilic carrier is PEG-32 stearate.

2. The solid pharmaceutical composition according to claim 1, wherein the composition is a solid dosage form selected from the group consisting of a tablet, a capsule, and a granule.

3. The solid pharmaceutical composition according to claim 1, further comprising an adsorbent selected from the group consisting of silicon dioxide, aluminum silicate, and mixtures thereof.

4. The solid pharmaceutical composition according to claim 1, wherein the composition is prepared by employing melt granulation, said melt granulation comprising melting and mixing of the solid carrier/hydrophilic carrier with a dispersion of telmisartan in a pH modifier solution, said melting and mixing being carried out in the presence of diluent.

5. The solid pharmaceutical composition according to claim 1, wherein the composition is prepared by employing both melt and wet granulation, by a process comprising,
   a) a step of melt granulation, comprising melting and mixing of the solid carrier/hydrophilic carrier with a dispersion of telmisartan in a pH modifier solution;
   b) granulating the product of step (a) using a granulating agent in the presence of a diluent;
   c) mixing behenoyl polyoxyl-8 glycerides, in combination with the superdisintegrant, with granules obtained in step (b); and
   d) compressing granules obtained in step (c) in controlled temperature and humidity conditions to get tablets.

6. The pharmaceutical composition according to claim 1, wherein the solid carrier/hydrophilic carrier has a melting point of 48° C., and an HLB value of 16.

7. A tablet comprising the pharmaceutical composition according to claim 1.

8. A capsule comprising the pharmaceutical composition according to claim 1.

* * * * *